US 6,569,438 B1

(12) United States Patent
Banowski et al.

(10) Patent No.: US 6,569,438 B1
(45) Date of Patent: May 27, 2003

(54) MULTIPHASE STICK PREPARATION

(75) Inventors: Bernhard Banowski, Duesseldorf (DE); Wolfhard Scholz, Krefeld (DE); Pascal Bordat, Mervilla (FR); Marion Pöppl, Kaarst (DE)

(73) Assignee: Henkel Kommanditgesellschaft auf Aktien, Duesseldorf (DE)

( * ) Notice: Subject to any disclaimer, the term of this patent is extended or adjusted under 35 U.S.C. 154(b) by 0 days.

(21) Appl. No.: 09/554,304

(22) PCT Filed: Oct. 30, 1998

(86) PCT No.: PCT/EP98/06892

§ 371 (c)(1),
(2), (4) Date: Feb. 14, 2001

(87) PCT Pub. No.: WO99/23998

PCT Pub. Date: May 20, 1999

(30) Foreign Application Priority Data

Nov. 11, 1997 (DE) .......................... 197 49 760

(51) Int. Cl.[7] .............................. A61K 7/00; A61K 7/32; A61K 7/021; A61K 7/035; A45D 40/20
(52) U.S. Cl. ........................ 424/401; 424/63; 424/64; 424/65; 424/68; 424/DIG. 5; 514/944; 514/951
(58) Field of Search .................. 424/401, 63, 64, 424/65, 68, DIG. 5; 514/944, 951

(56) References Cited

U.S. PATENT DOCUMENTS

| 2,970,083 A | * | 1/1961 | Bell | |
| 3,268,970 A | | 8/1966 | Kelly | ............................ 25/8 |
| 3,910,861 A | | 10/1975 | Wolvers et al. | ............... 260/78 |
| 4,094,946 A | | 6/1978 | Finkensiep et al. | ......... 264/171 |
| 4,120,948 A | | 10/1978 | Shelton | ...................... 424/66 |
| 4,694,063 A | | 9/1987 | Hilaire et al. | ................ 528/315 |
| 4,764,424 A | | 8/1988 | Ganga et al. | ................ 428/327 |
| 4,831,061 A | | 5/1989 | Hilaire et al. | .................. 521/56 |
| 4,927,860 A | | 5/1990 | Hilaire et al. | .................. 521/60 |
| 5,232,689 A | * | 8/1993 | Katsoulis et al. | ............ 424/401 |
| 5,264,207 A | | 11/1993 | Bommelaer et al. | .......... 424/69 |

FOREIGN PATENT DOCUMENTS

| AT | 198 501 | 7/1958 |
| DE | 1 122 221 | 1/1962 |
| DE | 21 60 135 | 6/1972 |
| DE | 25 26 917 | 11/1976 |
| DE | 27 52 420 | 6/1978 |
| EP | 105 657 | 4/1984 |
| EP | 192 515 | 8/1986 |
| EP | 196 972 | 10/1986 |
| EP | 303 530 | 2/1989 |
| EP | 409 690 | 1/1991 |
| EP | 466 986 | 1/1992 |
| EP | 0 701 812 | 3/1996 |

OTHER PUBLICATIONS

Derwent Accession Number:1998–002739, JP 09227114A, Sep. 2, 1997, Pigments for Colored Cosmetics, MORI S [MORRI], abstract.*

* cited by examiner

*Primary Examiner*—Frederick Krass
*Assistant Examiner*—Clinton Ostrup
(74) *Attorney, Agent, or Firm*—Stephen D. Harper; Daniel Ortiz; Gregory M. Hill

(57) ABSTRACT

An improved stick preparation is provided which is made up of at least two separate phases and at least one phase contains spherical polymer particles which can contain a pigment. The particles provide smoothness to the preparation and can be used to provide an interesting visual appearance to the stick.

23 Claims, No Drawings

MULTIPHASE STICK PREPARATION

FIELD OF THE INVENTION

This invention relates to a cosmetic and dermatological preparation in the form of a stick for applying a composition dimensionally stable at ambient temperature and spreadable at body temperature to the skin, this composition comprising two or more gel phases of different composition.

BACKGROUND OF THE INVENTION

Two-phase stick preparations based on alcoholic soap gels have been known for some time, cf. for example DE-AS 1 122 221. Preparations such as these make is possible to introduce individual constituents which are incompatible with other components into one phase of the stick and thus to prevent unwanted interactions with the components of the second phase. The storage stability of the stick preparations can also be increased by introducing the more readily volatile or oxidation-sensitive components into the core or into one of the inner phases of the stick.

However, problems arise out of the fact that the contact between the two phases can lead to interactions between the phases, more particularly to the bleeding of individual components into the other phase. In order to prevent this, DE-A-2 752 420 proposes a two-phase antiperspirant stick which comprises a core of an oil solidified with waxes and an outer phase or jacket of a polyol soap gel.

These known stick preparations are unsatisfactory both in their sensorial properties and in their performance properties. Above all, they do not solve the problem of effectively preventing individual components of two-phase soap gel sticks from bleeding from one phase into the other phase.

Another problem to be solved was to develop multiphase stick preparations with a particularly attractive, aesthetically satisfactory appearance and improved sensorial properties.

BRIEF DESCRIPTION OF THE INVENTION

According to the invention, this problem has been solved by dispersing a porous powder of spherical polymer particles in one of the gel phases. Microspheres such as these can also be charged with sensitive active ingredients, readily volatile perfumes or dyes so that these components are stabilized.

Accordingly, the present invention relates to a stick preparation of a composition which is dimensionally stable up to 40° C., can be spread onto the skin and melts at temperatures above 40° C. and which consists of two or more separate gel phases of different composition which contain monohydric or polyhydric alcohols, gelling agents, perfumes, cosmetic or dermatological principles and optionally water and galenic auxiliaries, a porous powder of spherical polymer particles being dispersed in one of the gel phases in a quantity of 0.1 to 10% by weight, based on that phase.

In addition, the stick preparation according to the invention can be made aesthetically very attractive through differences in the transparency, coloring or pigmenting of the phases. The spherical polymer particles improve skin feel where corresponding sticks are used on the skin by increasing the lubricating effect and reducing tackiness. Finally, it has been found that perfumes and cosmetic principles can be at least partly absorbed in the porous polymer particles and released to the skin again under control, i.e. over a prolonged period. This slow-release effect can be enhanced by initially charging the porous polymer particles during their production with the perfumes and active principles and introducing them thus charged into the gel phase.

In the context of the present invention, the expression "gel phase" is understood to be a composition which comprises a liquid phase that has been solidified by a gelling agent. The liquid phase may consist of water, monohydric and polyhydric alcohols containing 2 to 8 carbon atoms and mixtures thereof. Suitable agents for gelling these liquid phases are surfactants which, dissolved in the liquid phase, form a network structure and thus solidify the liquid phase to form the gel. Gelling agents such as these are, for example, the metal salts of fatty acids, preferably those containing 12 to 22 carbon atoms, fatty acid amides, fatty acid alkanolamides, dibenzal sorbitol and certain polymers, for example alcohol-soluble polyamides and polyacrylamides, or mixtures of these gelling agents. Preferred gelling agents are the alkali metal, alkaline earth metal, aluminium and amine soaps of $C_{12-22}$ fatty acids, for example sodium stearate, sodium palmitate, magnesium stearate or aluminium stearate.

Preferred polyhydric alcohols are polyols containing 2 to 8 carbon atoms and 2 to 6 hydroxyl groups, for example ethylene glycol, 1,2-propylene glycol, 1,3-propylene glycol, 1,2-butylene glycol, 1,3-butylene glycol, 1,4-butylene glycol, 2-methyl propane-1,3-diol, glycerol, erythritol, penta-erythritol, trimethylol propane, sorbitol, methyl glucoside, cyclohexane triol or inositol. Suitable monohydric alcohols are, for example, ethanol, n-propanol and isopropanol. Preferred components of the liquid phase are ethanol, 1,2-propylene glycol, butane-1,3-diol, glycerol, sorbitol and mixtures thereof, optionally even in admixture with water.

The gel phases additionally contain perfumes or cosmetic or dermatological principles.

Suitable perfumes or perfume oils include individual perfume compounds, for example synthetic products of the ester, ether, aldehyde, ketone, alcohol and hydrocarbon type. Perfume compounds of the ester type are, for example, benzyl acetate, phenoxyethyl isobutyrate, p-tert.butyl cyclohexyl acetate, linalyl acetate, dimethyl benzyl carbinyl acetate, phenyl ethyl acetate, linalyl benzoate, benzyl formate, ethyl methyl phenyl glycinate, allyl cyclohexyl propionate, styrallyl propionate and benzyl salicylate. The ethers include, for example, benzyl ethyl ether; the aldehydes include, for example, the linear alkanals containing 8 to 18 carbon atoms, citral, citronellal, citronellyloxyacetaldehyde, cyclamen aldehyde, hydroxycitronellal, lilial and bourgeonal; the ketones include, for example, the ionones, α-isomethyl ionone and methyl cedryl ketone; the alcohols include anethol, citronellol, eugenol, geraniol, linalool, phenyl ethyl alcohol and terpineol and the hydrocarbons include, above all, the terpenes and balsams. However, mixtures of various perfumes which together produce an attractive perfume note are preferably used.

Perfume oils such as these may also contain natural fragrance mixtures obtainable from vegetable or animal sources, for example pine, citrus, jasmine, lily, rose or ylang-ylang oil. Other suitable perfume oils are essential oils of relatively low volatility which are generally used as aroma components, for example sage oil, camomile oil, clove oil, melissa oil, mint oil, cinnamon leaf oil, lime blossom oil, juniper berry oil, vetiver oil, olibanum oil, galbanum oil and labdanum oil, Suitable cosmetic principles are, above all; substances which have a favorable effect on the aesthetic properties of the skin, more particularly on its smoothness and suppleness, on skin moisture, on perspiration and body odor and on the coloring or browning of the skin and on its protection against the harmful effects of the environment, more particularly sunlight.

Preferred cosmetic principles for the stick preparations according to the invention are, above all, deodorizing and perspiration-inhibiting substances. These are understood above all to be antimicrobial substances which have an inhibiting effect on perspiration-decomposing microorganisms or enzyme-inhibiting substances which inhibit the perspiration-decomposing esterase enzyme. Suitable antimicrobial agents are, for example, 2,4,4'-trichloro-2-2'-hydroxydiphenyl ether (Triclosan®), chlorhexidine gluconate, phenoxyethanol, pentane-1,5-diol, hexane-1,6-diol, antimicrobial essential oils and farnesol. Suitable lipase inhibitors are, for example, triethyl citrate and triacetin. Perspiration-inhibiting astringent substances compatible with the gel phase may also be present iii the stick preparations. Suitable antiperspirant agents are, for example, sodium aluminium chlorohydroxylactate, which is marketed under the name of Chloracel®, and other astringent substances.

Dermatological principles are generally understood to be substances which have a healing effect or preventive effect on diseases of the skin. Suitable dermatological agents are, for example, local anaesthetics, antibiotics, antiphlogistics, antiallergics, corticosteroids, sebostatic agents and other locally acting pharmaceutical agents.

Vitamins, panthenol, allantoin, plant extracts and proteins with dermatological activity, including for example octoxyglycerol, may also be present as active principles.

Porous powders of spherical polymer particles have long been used in cosmetics as a component of skin-care compositions because they have a favorable effect on the smoothness of the skin and can prevent tackiness (cf. EP 105 657 A1 and EP 409 690 B1). There are also various known processes for producing microspheres such as these from various monomers, for example by special polymerization processes or by dissolving the polymer in a solvent and spraying the solution into a medium in which the solvent is able to evaporate or to diffuse from the particles. One such process is known, for example, from EP 466 986 B1. Suitable polymers are, for example, polycarbonates, polyurethanes, polyacrylates, polyolefins, polyesters and polyamides.

The production of porous microspheres by special polymerization processes is described, for example, for polyamides in DE-A-2 160 125, EP 192 515 B1 and EP 303 530 B1. In the processes described in these documents, fillers, for example pigment particles, may also be added to the polymerization mixture so that porous microspheres of polyamides filled with fillers or pigment particles can be produced in this way. A process for producing microspheres from inert particles, for example pigments, coated with polyamide is also described in EP 196 972 B1.

Preferred porous powders of spherical polymer particles contain a core of a pigment particle, for example of titanium dioxide. Through polymer powders such as these, a white or colored, optionally pearlescent color effect can be introduced into the clear gel phase, providing the two-phase stick preparation according to the invention with an attractive appearance.

The porous powders of spherical polymer particles optionally comprising a pigment core preferably have a mean particle size of 0.5 to 50 µm and a specific surface of 1 to 20 m$^2$/g. Polymer powders such as these are commercially available, for example under the name of Microthene® (U.S.J. Chemicals) in the case of of polyethylene, under the name of Miralite® (Pierce & Stevens Chem. Corp.) in the case of polyvinylidene chloride or under the name of Orgasol® (ATOCHEM SA) in the case of polyamide (Nylon). Other known commercial products are, for example, polyacrylates (Polytrap®, Dow Corning), polymethacrylates (Micropearl®, SEPPIC), polyethylenes and polypropylenes (Accurel®, Akzo).

According to -the invention, a particularly preferred two-phase stick preparation contains spherical polymer particles with a core of pigment, preferably titanium dioxide, in a quantity of 30 to 60% by weight, based on particle weight. One such product based on polyamide is obtainable, for example, as Orgasol® 1002 Ex D Weiβ 10 Cos from Lehmann & Voss & Co., Hamburg.

The gel phases of the multiphase sticks according to the invention preferably consist of soap gels and contain 20 to 90% by weight of monohydric or polyhydric alcohols containing 2 to 6 carbon atoms, 4 to 14% by weight of fatty acids containing 12 to 22 carbon atoms in the form of their metal or amine soaps, 0.1 to 30% by weight of perfumes or cosmetic or dermatological principles and optionally water and typical galenic auxiliaries.

Typical galenic auxiliaries in the context of the invention are substances which are normally added to stick preparations of the type in question to influence consistency, transparency, abrasion or stability. Corresponding auxiliaries are, above all, surface-active substances, for example emulsifiers, solubilizers and dispersants. In addition, thickeners, for example water-soluble polymers, layer silicates, pyrogenic silica, electrolyte salts, such as KCl, NaCl, complexing agents, for example EDTA tetrasodium salt, and other auxiliaries are used.

The gel phases of the multiphase stick preparation according to the invention are preferably very similar in composition and, for the most part, differ only in their color, transparency, content of polymer powder and the active principles present therein.

In another preferred embodiment, the porous powder of spherical polymer particles is charged with perfumes or cosmetic or dermatological principles. This is preferably done by incorporating the microspheres in the gel in the form of a dispersion in monohydric or polyhydric alcohols in which the perfumes or active principles are also present.

A delayed release of the perfumes and active principles on the skin and hence a prolonging of the effect on the skin are achieved in this way. In addition, unwanted interaction with other components of the gel phase is prevented in this way.

Totally different or incompatible active principles may also be incorporated in the stick composition in this way providing part of the polymer powder is charged with one active principle and another part of the polymer powder is charged with another active principle and the polymer powders thus differently charged are introduced into the same phase of the stick composition.

In one particularly preferred embodiment, the stick composition is present in the form of two or more concentrically arranged phases of which the inner phase or one of the inner phases contain(s) the dispersed powder of spherical polymer particles. The outer phase is preferably transparent and optionally lightly colored. Aesthetically particularly attractive stick preparations are obtained in this way. Corresponding stick preparations can be produced, for example, by initially forming the core by pouring the gel liquefied by heating into a mold, allowing it to cool and gel, removing it from the mold, introducing it into a wider mold and then forming the outer phase or jacket by pouring the gel liquefied by heating into the space between the core and the mold wall, allowing it to cool and gel and removing it from the mold.

A similar process comprises initially forming the outer phase/jacket by pouring the liquefied gel into an annular mold with a removable cylindrical core, allowing it to cool and gel and removing the core and then pouring the liquefied gel of the core into the cylindrical space of the jacket thus formed and leaving it to harden.

In principle, the core does not have to be cylindrical in shape and may even assume the form of a cone or frustum or a helix. In order to simplify production, the phases may advantageously be arranged parallel to the longitudinal axis of the stick.

In this case, it is possible in principle to use the continuous processes known from the technology of soap production for producing multicolored soap strands of differently colored soap compositions in order to produce a single strand of two or more gels which can be cut into sticks of any length. Corresponding processes for producing strands of concentrically arranged phases are, for example, the coaxial extrusion processes known from AT-PS 198 501 and DE-AS 2 526 917. Other processes for producing multiphase strands of phases arranged parallel to the longitudinal axis (but not concentric phases) are described in U.S. Pat. No. 3,268,970.

The multiphase stick preparations produced in this way are preferably introduced into a tube with a bottom piston designed for displacement longitudinally of the tube axis by a pushing, turning or pressure mechanism of the type typically used for deodorant sticks and other cosmetic sticks. In this way, the stick can be conveniently handled without the fingers coming into direct contact with the stick.

The following Examples are intended to illustrate the invention.

EXAMPLES

| Formulations | K1 | K2 | K3 | K4 |
|---|---|---|---|---|
| Palmitic/stearic acid 12) | 6.50 | 4.80 | 7.00 | 7.00 |
| Isostearic acid 1) | — | 1.20 | — | — |
| Ethanol (96% by volume) denatured | 56.80 | — | 30.00 | 45.00 |
| 1,2-Propylene glycol | 29.17 | 30.00 | 26.01 | 36.40 |
| Butane-1,3-diol | — | — | — | — |
| Polyethylene glycol 400 | — | — | — | 5.00 |
| Glycerol, 86% | 2.60 | 46.00 | 26.40 | 3.00 |
| Sorbitol, 70% | — | 10.00 | — | — |
| Water | 2.15 | 4.10 | — | — |
| Fatty alcohol polyglycol ether 2) | — | — | — | — |
| Hydrogenated castor oil polyglycol ether 3) | — | — | — | — |
| Fatty alcohol polyglycol ether 4) | — | — | 3.00 | — |
| 2-Octyl dodecanol 5) | — | — | — | — |
| Sodium chloride | — | 0.15 | — | — |
| Ethylenediamine tetraacetic acid tetrasodium salt solution 6) | — | — | 0.20 | 0.20 |
| NaOH (pellets) | 0.98 | — | — | — |
| Sodium hydroxide, 45% | — | 2.05 | 2.39 | 2.40 |
| Triethanolamine | 0.20 | — | — | — |
| Phenoxyethanol | — | — | — | 0.50 |
| Triclosan | 0.10 | 0.20 | — | — |
| Farnesol | — | — | 0.50 | — |
| 3-(2-ethylhexyloxy)-propane-1,2-diol 7) | — | — | — | — |
| Perfume oil | 1.00 | 1.00 | 4.00 | — |
| Dye solution | — | — | — | — |
| Polymer powder B) | 0.50 | 0.50 | 0.50 | 0.50 |
| | 100.00 | 100.00 | 100.00 | 100.00 |

| Formulations | K5 | K6 | K7 | K8 |
|---|---|---|---|---|
| Palmitic/stearic acid 12) | 7.00 | 7.00 | 7.00 | 7.00 |
| Isostearic acid 1) | — | — | — | — |
| Ethanol (96% by volume) denatured | 45.00 | 40.00 | 50.00 | 40.00 |
| 1,2-Propylene glycol | 35.40 | 45.40 | 25.40 | 35.40 |
| Butane-1,3-diol | — | — | — | 10.00 |
| Polyethylene glycol 400 | — | — | — | — |
| Glycerol, 86% | 3.00 | 3.00 | 3.00 | 3.00 |
| Sorbitol, 70% | — | — | — | — |
| Water | 5.00 | — | 10.00 | — |
| Fatty alcohol polyglycol ether 2) | — | — | — | — |
| Hydrogenated castor oil polyglycol ether 3) | — | — | — | — |
| Fatty alcohol polyglycol ether 4) | — | — | — | — |
| 2-Octyl dodecanol 5) | — | — | — | — |
| Sodium chloride | — | — | — | — |
| Ethylenediamine tetraacetic acid tetrasodium salt solution 6) | 0.20 | 0.20 | 0.20 | 0.20 |
| NaOH (pellets) | — | — | — | — |
| Sodium hydroxide, 45% | 2.40 | 2.40 | 2.40 | 2.40 |
| Triethanolamine | — | — | — | — |
| Phenoxyethanol | 0.50 | 0.50 | 0.50 | 0.50 |
| Triclosan | — | — | — | — |
| Farnesol | — | — | — | — |
| 3-(2-ethylhexyloxy)-propane-1,2-diol 7) | — | — | — | — |
| Perfume oil | 1.00 | 1.00 | 1.00 | 1.00 |
| Dye solution | — | — | — | — |
| Polymer powder B) | 0.50 | 0.50 | 0.50 | 0.50 |
| | 100.00 | 100.00 | 100.00 | 100.00 |

| Formulations | K9 | K10 | K11 | K12 |
|---|---|---|---|---|
| Palmitic/stearic acid 12) | 4.50 | 7.00 | 4.50 | 4.50 |
| Isostearic acid 1) | — | — | — | — |
| Ethanol (96% by volume) denatured | 22.70 | 50.00 | 30.00 | 50.00 |
| 1,2-Propylene glycol | 20.91 | 34.10 | 37.75 | 17.95 |
| Butane-1,3-diol | 32.00 | — | 20.00 | 20.00 |
| Polyethylene glycol 400 | — | — | — | — |
| Glycerol, 86% | — | 3.00 | 3.00 | 3.00 |
| Sorbitol, 70% | — | — | — | — |
| Water | 9.70 | — | — | — |
| Fatty alcohol polyglycol ether 2) | 3.00 | — | — | — |
| Hydrogenated castor oil polyglycol ether 3) | 0.05 | — | — | — |
| Fatty alcohol polyglycol ether 4) | — | — | — | — |
| 2-Octyl dodecanol 5) | 2.00 | — | — | — |
| Sodium chloride | — | — | — | — |
| Ethylenediamine tetraacetic acid tetrasodium salt solution 6) | — | 0.20 | 0.20 | — |
| NaOH (pellets) | — | — | — | — |
| Sodium hydroxide, 45% | 1.54 | 2.40 | 1.55 | 1.55 |
| Triethanolamine | — | — | — | — |
| Phenoxyethanol | 1.00 | 1.00 | 0.50 | 0.50 |
| Triclosan | — | — | — | — |
| Farnesol | — | — | — | — |
| 3-(2-ethylhexyloxy)-propane-1,2-diol 7) | 0.30 | — | — | — |

| Formulations | K13 | K14 | K15 | K16 |
|---|---|---|---|---|
| Perfume oil | 2.00 | 2.00 | 1.50 | 1.50 |
| Dye solution | — | — | — | — |
| Polymer powder B) | 0.30 | 0.30 | 1.00 | 1.00 |
| | 100.00 | 100.00 | 100.00 | 100.00 |
| Palmitic/stearic acid 12) | 4.50 | 4.50 | 4.50 | 4.50 |
| Isostearic acid 1) | — | — | — | — |
| Ethanol (96% by volume) denatured | 50.00 | 40.00 | 40.00 | 22.70 |
| 1,2-Propylene glycol | 7.95 | 26.95 | 29.95 | 19.40 |
| Butane-1,3-diol | 30.00 | 20.00 | 20.00 | 32.00 |
| Polyethylene glycol 400 | — | — | — | — |
| Glycerol, 86% | 3.00 | 3.00 | — | — |
| Sorbitol, 70% | — | — | — | — |
| Water | — | — | — | 9.70 |
| Fatty alcohol polyglycol ether 2) | — | — | — | 5.00 |
| Hydrogenated castor oil polyglycol ether 3) | — | — | — | 0.05 |
| Fatty alcohol polyglycol ether 4) | — | 1.00 | 1.00 | — |
| 2-Octyl dodecanol 5) | — | — | — | 2.00 |
| Sodium chloride | — | — | — | — |
| Ethylenediamine tetra-acetic acid tetrasodium salt solution 6) | — | — | — | — |
| NaOH (pellets) | — | — | — | — |
| Sodium hydroxide, 45% | 1.55 | 1.55 | 1.55 | 1.55 |
| Triethanolamine | — | — | — | — |
| Phenoxyethanol | 0.50 | 0.50 | 0.50 | 0.50 |
| Triclosan | — | — | — | — |
| Farnesol | — | — | — | — |
| 3-(2-ethylhexyloxy)-propane-1,2-diol 7) | — | — | — | 0.30 |
| Perfume oil | 1.50 | 1.50 | 1.50 | 1.80 |
| Dye solution | — | — | — | — |
| Polymer powder 8) | 1.00 | 1.00 | 1.00 | 0.50 |
| | 100.00 | 100.00 | 100.00 | 100.00 |

| Formulations | K17 | K18 | K19 |
|---|---|---|---|
| Palmitic/stearic acid 12) | 7.50 | 4.50 | 4.60 |
| Isostearic acid 1) | — | — | — |
| Ethanol (96% by volume) denatured | — | — | 9.10 |
| 1,2-Propylene glycol | — | — | — |
| Butane-1,3-diol | 3.00 | 3.00 | 2.70 |
| Polyethylene glycol 400 | 42.83 | 45.65 | 42.00 |
| Glycerol, 86% | — | — | — |
| Sorbitol, 70% | — | — | — |
| Water | 38.50 | 39.80 | 35.49 |
| Silicone oil copolyol 9) | 2.00 | 2.00 | 1.80 |
| Fatty alcohol polyglycol ether 10) | 0.20 | 0.20 | 0.20 |
| Silicone oil 11) | 0.05 | 0.05 | 0.05 |
| 2-Octyl dodecanol 5) | — | — | — |
| NaOH (pellets) | — | — | — |
| Sodium hydroxide, 45% | 2.32 | 1.50 | 1.36 |
| Triethanolamine | — | — | — |
| Phenoxyethanol | 1.00 | 1.50 | 0.90 |
| Triclosan | — | — | — |
| Farnesol | — | — | — |
| 3-(2-ethylhexyloxy)-propane-1,2-diol 7) | 0.30 | 0.30 | 0.30 |
| Perfume oil | 2.00 | 1.20 | 1.10 |
| Dye solution | — | — | — |
| Polymer powder 8) | 0.30 | 0.30 | 0.40 |
| | 100.00 | 100.00 | 100.00 |

The following commercial products were used:
1) Emersol® 875
2) Aethoxal® B
3) Cremophor® RH455
4) Eumulgin® B3
5) Eutanol® G
6) Trilon® B
7) Sensiva® SC 50
8) Orgasol® 1002 EXD weiβ 10 COS
9) Abil® B8843
10) Brinj® 76
11) Silikonöl 100
12) Cutina® FS 45

| Formulations | H1 | H2 | H3 | H4 |
|---|---|---|---|---|
| Palmitic/stearic acid 12) | 6.50 | 4.80 | 7.00 | 7.00 |
| Isostearic acid 1) | — | 1.20 | — | — |
| Ethanol (96% by volume) denatured | 56.90 | — | 30.00 | 45.00 |
| 1,2-Propylene glycol | 29.17 | 30.00 | 26.51 | 36.60 |
| Butane-1,3-diol | — | — | — | — |
| Polyethylene glycol 400 | — | — | — | 5.00 |
| Glycerol, 86% | 2.60 | 46.00 | 26.40 | 3.00 |
| Sorbitol, 70% | — | 10.00 | — | — |
| Water | 2.15 | 4.38 | — | — |
| Fatty alcohol polyglycol ether 2) | — | — | — | — |
| Hydrogenated castor oil polyglycol ether 3) | — | — | — | — |
| Fatty alcohol polyglycol ether 4) | — | — | 3.00 | — |
| 2-Octyl dodecanol 5) | — | — | — | — |
| Sodium chloride | — | 0.15 | — | — |
| Ethylenediamine tetra-acetic acid tetrasodium salt solution 6) | — | — | 0.20 | 0.20 |
| NaOH (pellets) | 0.98 | — | — | — |
| Sodium hydroxide, 45% | — | 2.05 | 2.39 | 2.40 |
| Triethanolamine | 0.20 | — | — | — |
| Phenoxyethanol | — | — | — | 0.50 |
| Triclosan | 0.10 | 0.20 | — | — |
| Farnesol | — | — | 0.50 | — |
| 3-(2-ethylhexyloxy)-propane-1,2-diol 7) | — | — | — | — |
| Perfume oil | 1.00 | 1.00 | 4.00 | — |
| Dye solution | 0.40 | 0.22 | — | 0.30 |
| Polymer powder 8) | — | — | — | — |
| | 100.00 | 100.00 | 100.00 | 100.00 |

| Formulations | H5 | H6 | H7 | H8 |
|---|---|---|---|---|
| Palmitic/stearic acid 12) | 4.50 | 7.00 | 7.00 | 7.00 |
| Isostearic acid 1) | — | — | — | — |
| Ethanol (96% by volume) denatured | 22.70 | 50.00 | 45.00 | 40.00 |
| 1,2-Propylene glycol | 21.71 | 34.90 | 36.60 | 46.60 |
| Butane-1,3-diol | 32.00 | — | — | — |
| Polyethylene glycol 400 | — | — | — | — |
| Glycerol, 86% | — | 3.00 | 3.00 | 3.00 |
| Sorbitol, 70% | — | — | — | — |
| Water | 9.70 | — | 5.00 | — |
| Fatty alcohol polyglycol ether 2) | 3.00 | — | — | — |
| Hydrogenated castor oil polyglycol ether 3) | 0.05 | — | — | — |
| Fatty alcohol polyglycol ether 4) | — | — | — | — |
| 2-Octyl dodecanol 5) | 2.00 | — | — | — |
| Sodium chloride | — | — | — | — |
| Ethylenediamine tetra-acetic acid tetrasodium salt solution 6) | — | 0.20 | 0.20 | 0.20 |
| NaOH (pellets) | — | — | — | — |
| Sodium hydroxide, 45% | 1.54 | 2.40 | 2.40 | 2.40 |
| Triethanolamine | — | — | — | — |
| Phenoxyethanol | 0.50 | 0.50 | 0.50 | 0.50 |
| Triclosan | — | — | — | — |
| Farnesol | — | — | — | — |
| 3-(2-ethylhexyloxy)- | 0.30 | | | |

-continued

| | H5 | H6 | H7 | H8 |
|---|---|---|---|---|
| propane-1,2-diol 7) | | | | |
| Perfume oil | 1.50 | 1.50 | — | — |
| Dye solution | 0.50 | 0.50 | 0.30 | 0.30 |
| Polymer powder 8) | — | — | — | — |
| | 100.00 | 100.00 | 100.00 | 100.00 |

| Formulations | H9 | H10 | H11 | H12 |
|---|---|---|---|---|
| Palmitic/stearic acid 12) | 7.00 | 7.00 | 4.50 | 4.50 |
| Isostearic acid 1) | — | — | — | — |
| Ethanol (96% by volume) denatured | 50.00 | 40.00 | 30.00 | 50.00 |
| 1,2-Propylene glycol | 26.60 | 36.60 | 40.25 | 20.45 |
| Butane-1,3-diol | — | 10.00 | 20.00 | 20.00 |
| Polyethylene glycol 400 | — | — | — | — |
| Glycerol 86% | 3.00 | 3.00 | 3.00 | 3.00 |
| Sorbitol, 70% | — | — | — | — |
| Water | 10.00 | — | — | — |
| Fatty alcohol polyglycol ether 2) | — | — | — | — |
| Hydrogenated castor oil polyglycol ether 3) | — | — | — | — |
| Fatty alcohol polyglycol ether 4) | — | — | — | — |
| 2-Octyl dodecanol 5) | — | — | — | — |
| Sodium chloride | — | — | — | — |
| Ethylenediamine tetraacetic acid tetrasodium salt solution 6) | 0.20 | 0.20 | 0.20 | — |
| NaOH (pellets) | — | — | — | — |
| Sodium hydroxide, 45% | 2.40 | 2.40 | 1.55 | 1.55 |
| Triethanolamine | — | — | — | — |
| Phenoxyethanol | 0.50 | 0.50 | 0.50 | 0.50 |
| Triclosan | — | — | — | — |
| Farnesol | — | — | — | — |
| 3-(2-ethylhexyloxy)-propane-1,2-diol 7) | — | — | — | — |
| Perfume oil | — | — | — | — |
| Dye solution | 0.30 | 0.30 | — | — |
| Polymer powder B) | — | — | — | — |
| | 100.00 | 100.00 | 100.00 | 100.00 |

| Formulations | H13 | H14 | H15 |
|---|---|---|---|
| Palmitic/stearic acid 12) | 4.50 | 4.50 | 4.50 |
| Isostearic acid 1) | — | — | — |
| Ethanol (96% by volume) denatured | 50.00 | 40.00 | 40.00 |
| 1,2-Propylene glycol | 10.45 | 29.45 | 32.45 |
| Butane-1,3-diol | 30.00 | 20.0 | 20.00 |
| Polyethylene glycol 400 | — | — | — |
| Glycerol 86% | 3.00 | 3.00 | — |
| Sorbitol, 70% | — | — | — |
| Water | — | — | — |
| Fatty alcohol polyglycol ether 2) | — | 1.00 | 1.00 |
| Hydrogenated castor oil polyglycol ether 3) | — | — | — |
| Fatty alcohol polyglycol ether 4) | — | 1.00 | 1.00 |
| 2-Octyl dodecanol 5) | — | — | — |
| Sodium chloride | — | — | — |
| Ethylenediamine tetraacetic acid tetrasodium salt solution 6) | — | — | — |
| NaOH (pellets) | — | — | — |
| Sodium hydroxide, 45% | 1.55 | 1.55 | 1.55 |
| Triethanolamine | — | — | — |
| Phenoxyethanol | 0.50 | 0.50 | 0.50 |
| Triclosan | — | — | — |
| Farnesol | — | — | — |
| 3-(2-ethylhexyloxy)-propane-1,2-diol 7) | — | — | — |
| Perfume oil | — | — | — |
| Dye solution | — | — | — |
| Polymer powder 8) | — | — | — |
| | 100.00 | 100.00 | 100.00 |

1. Production of the Stick Compositions Containing Polymer Powders K1 to K19

First a premix was prepared from 0.3 part by weight Orgasol® 1002 EXD weiβ 10 COS
0.7 part by weight 1,2-propylene glycol
1.0 part by weight phenoxyethanol
0.3 part by weight 3-(2-ethylhexyloxy)-propane-1,2-diol and
1.0 part by weight perfume oil.

The premix was obtained in the form of a white flowable paste.

Fatty acid, ethanol and the remaining polyols and oil components were mixed and heated to 65° C., after which the 45% aqueous sodium hydroxide also heated to 65° C. was added. Saponification was carried out with stirring at 65° C. After complete saponification of the fatty acid, the premix, the remaining perfume oil and the other components were stirred in. The mixture was then introduced into prepared cylindrical molds of which the diameter was ca. 60% of the diameter of a commercially available cosmetic stick.

The stick was demolded after cooling to 15° C.

2. Production of Stick Compositions H1 to H15

These stick compositions were produced in the same way as normal soap gel sticks.

3. Production of a Two-phase Deodorant Stick

A demolded stick composition based on formulation K4 was centrally introduced as core into a standard stick tube. Stick composition H4 was then prepared and poured at 65° C. into the space between the core and the tube wall.

After the closure caps had been screwed on, the stick tubes were inverted, i.e. turned upside-down, so that the stick composition which had not yet solidified formed a smooth surface in the closure cap.

After cooling, an attractive-looking two-phase stick with a transparent lightly colored outer phase and a white core was obtained.

Two-phase sticks were produced in the same way from the following stick compositions:

| K6 | (core) + H4 | (jacket) | K8 | (core) + H10 | (jacket) |
|---|---|---|---|---|---|
| K8 | (core) + H4 | (jacket) | K5 | (core) + H4 | (jacket) |
| K10 | (core) + H4 | (jacket) | K7 | (core) + H15 | (jacket) |
| K15 | (core) + H5 | (jacket) | K9 | (core) + H5 | (jacket) |
| K4 | (core) + H6 | (jacket) | K11 | (core) + H5 | (jacket) |
| K6 | (core) + H6 | (jacket) | K18 | (core) + H5 | (jacket) |
| K9 | (core) + H6 | (jacket) | K5 | (core) + H6 | (jacket) |
| K6 | (core) + H8 | (jacket) | K8 | (core) + H6 | (jacket) |
| K4 | (core) + H10 | (jacket) | K10 | (core) + H6 | (jacket) |
| K8 | (core) + H8 | (jacket) | K8 | (core) + H8 | (jacket) |
| K5 | (core) + H10 | (jacket) | K10 | (core) + H10 | (jacket) |

Two-phase sticks with a clearly discernible core in a transparent jacket were obtained in every case and had not changed in any way after several weeks at 25° C.

What is claimed is:

1. A stick preparation of a composition which is dimensionally stable tip to 40° C., can be spread onto the skin and melts at temperatures above 40° C. which comprises at least two separate gel phases of different compositions which gel phases comprise:
- (a) at least one member selected from the group consisting of monohydric alcohols, polyhydric alcohols, and mixtures thereof;
- (b) at least one gelling agent; and
- (c) at least one perfume, cosmetic principle or dermatological principle, or mixtures thereof, wherein a powder comprising spherical porous polymer particles is dispersed in at least one of the gel phases in a quantity of 0.1% to 10% by weight, based on the total weight of that phase.

2. The stick preparation as claimed in claim 1, which comprises at least two concentric phases of which an inner phase comprises the dispersed powder of spherical porous polymer particles.

3. The stick preparation of claim 2 wherein each of the phases comprise, based on the total weight of that phase:
- (a) 20% to 90% by weight of the at least one monohydric or polyhydric alcohol selected from the group consisting of monohydric alcohols containing 2 to 6 carbon atoms, polyhydric alcohols containing 2 to 6 carbon atoms and mixtures thereof,
- (b) 4% to 14% by weight of the at least one gelling agent selected from one or more fatty acids containing 12 to 22 carbon atoms in the form of their metal or amine soaps; and
- (c) 0.1% to 30% by weight of the at least one perfume, cosmetic principle, or dermatological principle or mixtures thereof.

4. The stick preparation of claim 2 wherein the composition comprises at least one cosmetic principle selected from at least one deodorizing agent or perspiration-inhibiting agent or mixtures thereof.

5. A process for producing a stick preparation as claimed in claim 2 wherein the powder of spherical porous polymer particles is charged with at least a portion of the perfume, cosmetic principle or dermatological principle by forming a dispersion comprising the spherical polymer particles, at least part of the monohydric or polyhydric alcohol, and the perfume, cosmetic principle or dermatological principle to be charged and incorporating the dispersion formed in at least one of the gel phases.

6. The stick preparation of claim 2 wherein the spherical polymer particles comprise a core of a pigment, in a quantity of 30 to 60% by weight, based on the particle weight.

7. The stick preparation of claim 6 wherein the pigment comprises titanium dioxide.

8. The stick preparation as claimed in claim 1 wherein each of tie phases comprise, based on the total weight of that phase:
- (a) 20% to 90% by weight of the at least one monohydric or polyhydric alcohol selected from the group consisting of monohydric alcohols containing 2 to 6 carbon atoms, polyhydric alcohols containing 2 to 6 carbon atoms and mixtures thereof;
- (b) 4% to 14% by weight of the at least one gelling agent selected from one or more fatty acids containing 12 to 22 carbon atoms in the form of heir metal or amine soaps; and
- (c) 0.1% to 30% by weight of the at least one perfume, cosmetic principle, or dermatological principle or mixtures thereof.

9. The stick preparation of claim 8 wherein the composition comprises at least one cosmetic principle selected from at least one deodorizing agent or perspiration-inhibiting agent or mixtures thereof.

10. A process for producing a stick preparation as claimed in claim 8 wherein the powder of spherical porous polymer particles is charged with at least a portion of the perfume, cosmetic principle or dermatological principle by forming a dispersion comprising the spherical polymer particles, at least part of the monohydric or polyhydric alcohol, and the perfume, cosmetic principle or dermatological principle to be charged and incorporating the dispersion formed in at least one of the gel phases.

11. The stick preparation of claim 8 wherein the spherical polymer particles comprise a core of a pigment, in a quantity of 30 to 60% by weight, based on the particle weight.

12. The stick preparation of claim 11 wherein the pigment comprises titanium dioxide.

13. The stick preparation as claimed in claim 1 wherein the spherical polymer particles comprise a core of a pigment, in a quantity of 30 to 60% by weight, based on the particle weight.

14. The stick preparation of claim 13 wherein the pigment comprises titanium dioxide.

15. The stick preparation of claim 13 wherein the composition comprises at least one cosmetic principle selected from at least one deodorizing agent or perspiration-inhibiting agent or mixtures thereof.

16. A process for producing a stick preparation as claimed in claim 13 wherein the powder of spherical porous polymer particles is charged with at least a portion of the perfume, cosmetic principle or dermatological principle by forming a dispersion comprising the spherical polymer particles, at least part of the monohydric or polyhydric alcohol, and the perfume, cosmetic principle or dermatological principle to be charged and incorporating the dispersion formed in at least one of the gel phases.

17. The stick preparation as claimed in claim 1 wherein the composition comprises at least one cosmetic principle selected from at least one deodorizing agent or perspiration-inhibiting agent or mixtures thereof.

18. A process for producing a stick preparation as claimed in claim 17 wherein the powder of spherical porous polymer particles is charged with at least a portion of the perfume, cosmetic principle or dermatological principle by forming a dispersion comprising the spherical polymer particles, at least part of the monohydric or polyhydric alcohol, and the perfume, cosmetic principle or dermatological principle to be charged and incorporating the dispersion formed in at least one of the gel phases.

19. A process for producing a stick preparation claimed in claim 1 wherein the powder of spherical porous polymer particles is charged with at least a portion of the perfume, cosmetic principle or dermatological principle by forming a dispersion comprising the spherical polymer particles, at least part of the monohydric or polyhydric alcohol, and the perfume, cosmetic principle or dermatological principle to be charged and incorporating the dispersion formed in at least one of the gel phases.

20. The stick preparation of claim 1 wherein the porous polymer particles have a mean particle size in the range of 0.5 $\mu$m to 50 $\mu$m and a specific surface area of from 1 m$^2$/g to 20 m$^2$/g.

21. The stick preparation of claim 1 wherein at least one of the gel phases further comprise water or one or more galenic auxiliaries or mixtures thereof.

22. The stick preparation of claim 21 wherein the galenic auxiliaries are selected from surface-active substances, thickeners, complexing agents or combinations thereof.

23. The stick preparation of claim 1 wherein the porous polymer particles are comprised of one or more polycarbonates, polyurethanes, polyacrylates, polymethacrylates, polyolefins, polyesters, polyamides, or polyvinylidene chloride, or combinations thereof.

* * * * *

UNITED STATES PATENT AND TRADEMARK OFFICE
CERTIFICATE OF CORRECTION

PATENT NO. : 6,569,438 B1
DATED : May 27, 2003
INVENTOR(S) : Banowski et al.

It is certified that error appears in the above-identified patent and that said Letters Patent is hereby corrected as shown below:

Column 10,
Line 67, delete "tip" and insert therefore -- up --.

Column 11,
Line 25, after "thereof", delete "," and insert therefore -- ; --
Line 52, delete "tie" and insert therefore -- the --
Line 61, delete "heir" and insert therefore -- their --

Signed and Sealed this

Second Day of November, 2004

JON W. DUDAS
*Director of the United States Patent and Trademark Office*